US012765939B2

(12) United States Patent
Zagatsky

(10) Patent No.: US 12,765,939 B2
(45) Date of Patent: Oct. 20, 2026

(54) ELECTROSURGICAL DEVICE, METHODS OF MAKING AN ELECTROSURGICAL DEVICE, AND METHODS OF USING AN ELECTROSURGICAL DEVICE

(71) Applicant: Invuity, Inc., San Francisco, CA (US)

(72) Inventor: Vladimir Zagatsky, San Francisco, CA (US)

(73) Assignee: Stryker Corporation, Portage, MI (US)

( * ) Notice: Subject to any disclaimer, the term of this patent is extended or adjusted under 35 U.S.C. 154(b) by 1115 days.

(21) Appl. No.: 17/271,783

(22) PCT Filed: Aug. 27, 2019

(86) PCT No.: PCT/US2019/048326

§ 371 (c)(1),
(2) Date: Feb. 26, 2021

(87) PCT Pub. No.: WO2020/046921

PCT Pub. Date: Mar. 5, 2020

(65) Prior Publication Data

US 2021/0338310 A1 Nov. 4, 2021

Related U.S. Application Data

(60) Provisional application No. 62/723,054, filed on Aug. 27, 2018.

(51) Int. Cl.

| | |
|---|---|
| ***A61B 18/14*** | (2006.01) |
| *A61B 17/00* | (2006.01) |
| *A61B 18/00* | (2006.01) |

(52) U.S. Cl.

CPC *A61B 18/1402* (2013.01); *A61B 2017/00991* (2013.01); *A61B 2018/00136* (2013.01);

(Continued)

(58) Field of Classification Search

CPC ...... A61B 18/1402; A61B 2017/00991; A61B 2018/00136; A61B 2018/00589;

(Continued)

(56) References Cited

U.S. PATENT DOCUMENTS

| | | | | |
|---|---|---|---|---|
| 5,221,279 A * | 6/1993 | Cook | A61B 18/20 606/15 |
| 2003/0233037 A1* | 12/2003 | Bencini | A61B 18/1492 600/374 |

(Continued)

FOREIGN PATENT DOCUMENTS

| | | |
|---|---|---|
| CN | 101141995 A | 3/2008 |
| CN | 102750852 A | 10/2012 |

(Continued)

OTHER PUBLICATIONS

International Search Report mailed on Nov. 19, 2019, issued in connection with International Application No. PCT/US2019/048326, filed on Aug. 27, 2019, 5 pages.

(Continued)

*Primary Examiner* — Joanne M Rodden
*Assistant Examiner* — Abigail M Ziegler
(74) *Attorney, Agent, or Firm* — McDonnell Boehnen Hulbert & Berghoff LLP

(57) ABSTRACT

In an example, an electrosurgical device includes a housing defining an interior bore. The electrosurgical device also includes a shaft telescopically moveable in the interior bore of the housing, an electrosurgical blade coupled to the shaft, and a helical conductor coiled around the shaft and configured to supply electrosurgical energy from an electrosurgical generator to the electrosurgical blade.

20 Claims, 7 Drawing Sheets

(52) U.S. Cl.
CPC ............... *A61B 2018/00589* (2013.01); *A61B 2018/00601* (2013.01); *A61B 2018/1412* (2013.01)

(58) Field of Classification Search
CPC .. A61B 2018/00601; A61B 2018/1412; A61B 2218/007; A61B 2018/00595; A61B 2018/00607; A61B 2018/00619; A61B 2018/0063
See application file for complete search history.

(56) References Cited

U.S. PATENT DOCUMENTS

| | | | | |
|---|---|---|---|---|
| 2004/0116922 | A1 | 6/2004 | Hovda et al. | |
| 2006/0217655 | A1 | 9/2006 | Vitullo et al. | |
| 2006/0264928 | A1 | 11/2006 | Kornerup et al. | |
| 2010/0146897 | A1 | 6/2010 | Rodriguez et al. | |
| 2012/0172905 | A1 | 7/2012 | Lee Shee et al. | |
| 2014/0276797 | A1* | 9/2014 | Batchelor .......... | A61B 18/1445<br>606/42 |
| 2016/0157920 | A1 | 6/2016 | Vayser et al. | |
| 2017/0196634 | A1* | 7/2017 | Nagtegaal .......... | A61B 17/2909 |
| 2018/0177548 | A1 | 6/2018 | Ku et al. | |
| 2018/0333194 | A1* | 11/2018 | Greep ................ | A61B 18/1402 |
| 2019/0216539 | A1* | 7/2019 | Choi .................. | A61B 18/1402 |

FOREIGN PATENT DOCUMENTS

| | | | |
|---|---|---|---|
| CN | 103281974 | A | 9/2013 |
| CN | 204500939 | U | 7/2015 |
| CN | 105848601 | A | 8/2016 |
| CN | 205964153 | U | 2/2017 |
| CN | 106999716 | A | 8/2017 |
| JP | 2009264818 | A | 11/2009 |
| JP | 2015123117 | A | 7/2015 |
| TW | M284834 | U | 1/2006 |

OTHER PUBLICATIONS

Written Opinion mailed on Nov. 19, 2019, issued in connection with International Application No. PCT/US2019/048326, filed on Aug. 27, 2019, 9 pages.

* cited by examiner

ELECTROSURGICAL DEVICE, METHODS OF MAKING AN ELECTROSURGICAL DEVICE, AND METHODS OF USING AN ELECTROSURGICAL DEVICE

CROSS-REFERENCE TO RELATED APPLICATION

This present application is the US national phase under 35 U.S.C. § 371 of International Application No. PCT/US2019/048326, filed Aug. 27, 2019, which claims the benefit of priority of U.S. Provisional Patent Application No. 62/723,054, filed Aug. 27, 2018, the contents of which are hereby incorporated by reference in their entirety.

FIELD

The present disclosure generally relates to methods and apparatus for conveying electrical energy and, more specifically, to electrosurgical devices and the methods providing for telescopic adjustment of an electrosurgical blade.

BACKGROUND

Electrosurgery involves applying a radio frequency (RF) electric current (also referred to as electrosurgical energy) to biological tissue to cut, coagulate, or modify the biological tissue during an electrosurgical procedure. Specifically, an electrosurgical generator generates and provides the electric current to an active electrode, which applies the electric current (and, thus, electrical power) to the tissue. The electric current passes through the tissue and returns to the generator via a return electrode (also referred to as a "dispersive electrode"). As the electric current passes through the tissue, an impedance of the tissue converts a portion of the electric current into thermal energy (e.g., via the principles of resistive heating), which increases a temperature of the tissue and induces modifications to the tissue (e.g., cutting, coagulating, ablating, and/or sealing the tissue).

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Figure 1:
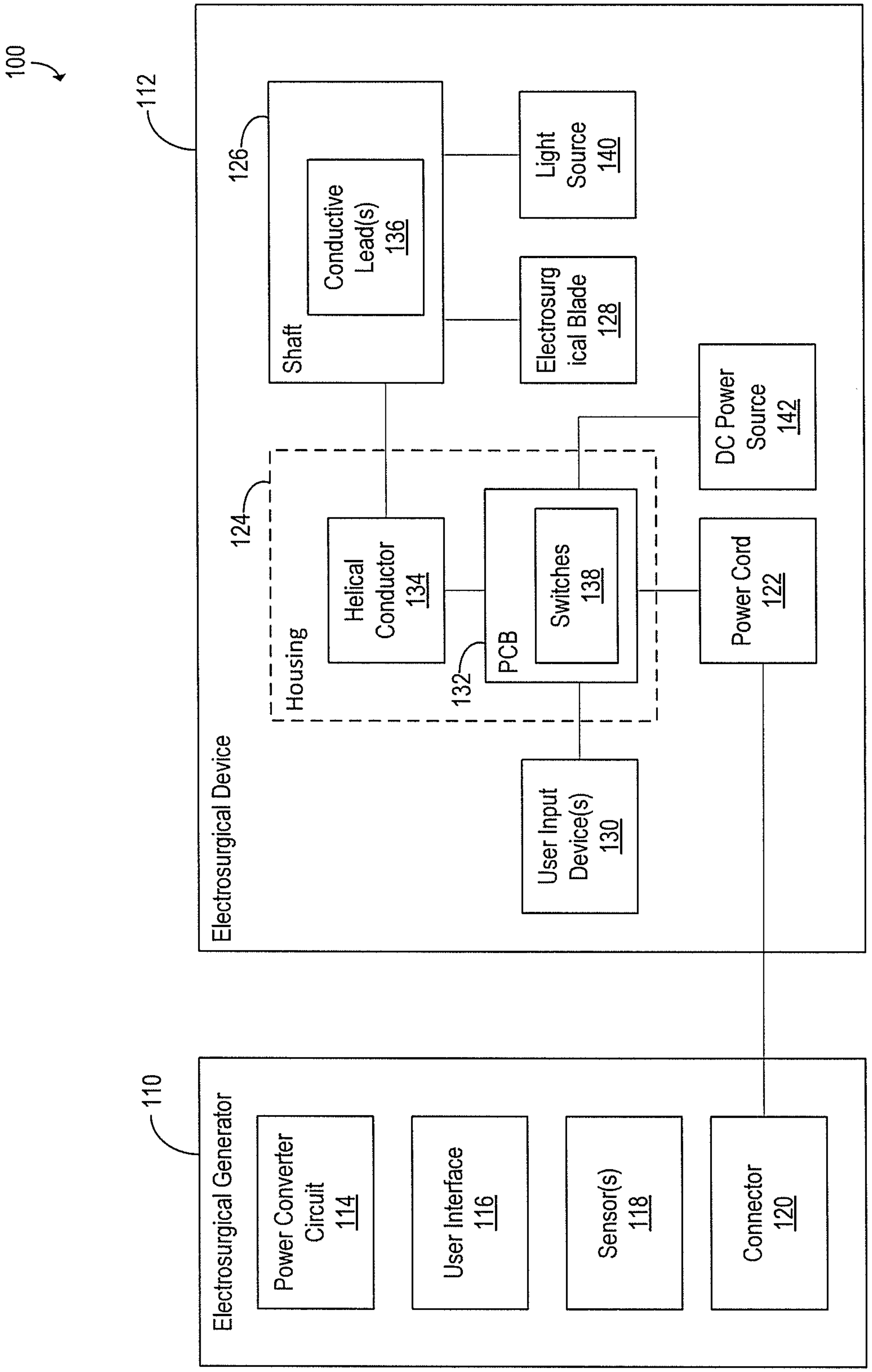
FIG. 1 depicts a simplified block diagram of an electrosurgical system, according to an example.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

By the term "approximately" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As noted above, an electrosurgical device can use electrical energy supplied by an electrosurgical generator to apply electrosurgical energy from an electrosurgical blade to a tissue. As such, the electrosurgical device generally includes a housing in which one or more conductors are disposed for supplying the electrosurgical energy to the electrosurgical blade. Some electrosurgical devices include a shaft that is telescopically adjustable relative to the housing. This can facilitate adjusting a length of the electrosurgical device to treat differently sized and/or shaped target tissues. This can present a challenge in that the electrical conductors may need to move relative to each other to accommodate the movement of the shaft relative to the housing.

One approach to conducting electrosurgical energy to the electrosurgical blade of such electrosurgical devices includes providing the electrosurgical device with a plurality of stamped metal parts that are slidably arranged relative to each other. However, this approach can be costly to manufacture and/or labor intensive to assembly.

The present disclosure describes an electrosurgical device that can address one or more of the challenges associated with prior approaches to supplying electrosurgical energy to the electrosurgical blade of a telescopically adjustable electrosurgical device. Within examples, the electrosurgical device includes a housing defining an interior bore, a shaft telescopically moveable in the interior bore of the housing, an electrosurgical blade coupled to the shaft, and a helical conductor coiled around the shaft and configured to supply electrosurgical energy from an electrosurgical generator to the electrosurgical blade. In this arrangement, the helical conductor can be compressible and expandable such that the helical conductor can accommodate the shaft telescopically moving into and/or out of the housing to retract and/or extend, respectively, the electrosurgical blade relative to the housing.

In an example, an electrosurgical device is described. The electrosurgical device includes a housing defining an interior bore. The electrosurgical device also includes a shaft telescopically moveable in the interior bore of the housing, an electrosurgical blade coupled to the shaft, and a helical conductor coiled around the shaft and configured to supply electrosurgical energy from an electrosurgical generator to the electrosurgical blade.

In another example, a method of making an electrosurgical device is described. The method includes forming a housing defining an interior bore, coupling a shaft to the interior bore of the housing such that the shaft is telescopically moveable in the interior bore of the housing, coupling an electrosurgical blade to the shaft, and coiling a helical conductor around the shaft to form a helical shape of the helical conductor. The helical conductor is configured to supply an electrosurgical energy from an electrosurgical generator to the electrosurgical blade.

In another example, a method of using an electrosurgical device is described. The method includes providing an electrosurgical device. The electrosurgical device includes a housing defining an interior bore, a shaft telescopically moveable in the interior bore of the housing, an electrosurgical blade coupled to the shaft, and a helical conductor coiled around the shaft. The method also includes telescopically moving the shaft relative to the housing such that (i) a position of a distal end of the helical conductor remains fixed relative to the housing and (ii) a position of a proximal end of the helical conductor translates relative to the housing. The method further includes coupling the electrosurgical device to an electrosurgical generator. Additionally, the method includes supplying, via the helical conductor, electrosurgical energy from the electrosurgical generator to the electrosurgical blade.

Referring now to FIG. 1, an electrosurgical system 100 is shown according to an example. As shown in FIG. 1, the electrosurgical system 100 includes an electrosurgical generator 110 and an electrosurgical device 112. In general, the electrosurgical generator 110 can generate electrosurgical energy that is suitable for performing electrosurgery on a patient. For instance, the electrosurgical generator 110 can include a power converter circuit 114 that can convert a grid power to electrosurgical energy such as, for example, a radio frequency (RF) output power. As an example, the power converter circuit 114 can include one or more electrical components (e.g., one or more transformers) that can control a voltage, a current, and/or a frequency of the electrosurgical energy.

Within examples, the electrosurgical generator 110 can include a user interface 116 that can receive one or more inputs from a user and/or provide one or more outputs to the user. As examples, the user interface 116 can include one or more buttons, one or more switches, one or more dials, one or more keypads, one or more touchscreens, and/or one or more display screens.

In an example, the user interface 116 can be operable to select a mode of operation from among a plurality of modes of operation for the electrosurgical generator 110. As examples, the modes of operation can include a cutting mode, a coagulating mode, an ablating mode, and/or a sealing mode. In one implementation, the modes of operation can correspond to respective waveforms for the electrosurgical energy. As such, in this implementation, the electrosurgical generator 110 can generate the electrosurgical energy with a waveform selected from a plurality of waveforms based, at least in part, on the mode of operation selected using the user interface 116.

The electrosurgical generator 110 can also include one or more sensors 118 that can sense one or more conditions related to the electrosurgical energy and/or the target tissue. As examples, the sensor(s) 118 can include one or more current sensors, one or more voltage sensors, and/or one or more temperature sensors. Within examples, the electrosurgical generator 110 can additionally or alternatively generate the electrosurgical energy with an amount of electrosurgical energy (e.g., an electrical power) and/or a waveform selected from among the plurality of waveforms based on one or more parameters related to the condition(s) sensed by the sensor(s) 118.

In one example, the electrosurgical energy can have a frequency that is greater than approximately 100 kilohertz (KHz) to reduce (or avoid) stimulating a muscle and/or a nerve near the target tissue. In another example, the electrosurgical energy can have a frequency that is between approximately 300 kHz and approximately 500 kHz.

In FIG. 1, the electrosurgical generator 110 also includes a connector 120 that can facilitate coupling the electrosurgical generator 110 to the electrosurgical device 112. For example, the electrosurgical device 112 can include a power cord 122 having a plug, which can be coupled to a socket of the connector 120 of the electrosurgical generator 110. In this arrangement, the electrosurgical generator 110 can supply the electrosurgical energy to the electrosurgical device 112 via the coupling between the connector 120 of the electrosurgical generator 110 and the power cord 122 of the electrosurgical device 112.

As shown in FIG. 1, the electrosurgical device 112 can include a housing 124 defining an interior bore, a shaft 126 telescopically moveable in the interior bore of the housing 124, and an electrosurgical blade 128 coupled to the shaft 126. In general, the housing 124 can be configured to facilitate a user gripping and manipulating the electrosurgical device 112 while performing electrosurgery. For example, the housing 124 can have a shape and/or a size that can facilitate a user performing electrosurgery by manipulating the electrosurgical device 112 using a single hand. In one implementation, the housing 124 can have a shape and/or a size that facilitates the user holding the electrosurgical device 112 in a writing utensil gripping manner (e.g., the electrosurgical device 112 can be an electrosurgical pencil).

Additionally, for example, the housing 124 can be constructed from one or more materials that are electrical insulators (e.g., a plastic material). This can facilitate insulating the user from the electrosurgical energy flowing through the electrosurgical device 112 while performing the electrosurgery.

As noted above, the shaft 126 is telescopically moveable relative to the housing 124 and the electrosurgical blade 128 is coupled to the shaft 126 (e.g., movable along a longitudinal axis of the electrosurgical device 112). This can provide for adjusting a length of the electrosurgical device 112, which can facilitate performing electrosurgery at a plurality of different depths within tissue (e.g., due to different anatomical shapes and/or sizes of patients) and/or at a plurality of different angles. In some examples, the shaft 126 can be rotatable about an axis of rotation that is parallel to the longitudinal axis of the electrosurgical device 112. This can provide for adjusting an angle of the electrosurgical blade 128 relative to one or more user input devices 130 of the electrosurgical device 112.

The user input device(s) 130 can select between the modes of operation of the electrosurgical device 112 and/or the electrosurgical generator 110. For instance, in one implementation, the user input device(s) 130 can be configured to select between a cutting mode of operation and a coagulation mode of operation. Responsive to actuation of the user input device(s) 130 of the electrosurgical device 112, the electrosurgical device 112 can (i) receive the electrosurgical energy with a level of power and/or a waveform corresponding to the mode of operation selected via the user input device(s) 130 and (ii) supply the electrosurgical energy to the electrosurgical blade 128.

In FIG. 1, the electrosurgical device 112 includes a plurality of electrical components that facilitate supplying the electrosurgical energy, which the electrosurgical device 112 receives from the electrosurgical generator 110, to the electrosurgical blade 128. For example, the electrosurgical device 112 can include a printed circuit board 132 (e.g., a flexible printed circuit board), a helical conductor 134, and/or one or more conductive leads 136 that can provide a circuit for conducting the electrosurgical energy from the power cord 122 to the electrosurgical blade 128.

Within examples, the user input device(s) 130 can include one or more buttons on an exterior surface of the housing 124. Each button of the user input device(s) 130 can be operable to actuate a respective one of a plurality of switches 138 of the printed circuit board 132. In general, the switches 138 and/or the printed circuit board 132 are operable to control a supply of the electrosurgical energy from the electrosurgical generator 110 to the electrosurgical blade 128. For instance, in one implementation, when each button is operated (e.g., depressed), the respective switch 138 associated with the button can be actuated to cause the printed circuit board 132 to transmit a signal to the electrosurgical generator 110 and cause the electrosurgical generator 110 to responsively supply the electrosurgical energy with a level of power and/or a waveform corresponding to a mode of operation associated with the button. In another implementation, operating the button and thereby actuating the respective switch 138 associated with the button can close the switch 138 to complete a circuit to electrosurgical generator 110 to cause the electrosurgical generator 110 to responsively supply the electrosurgical energy with a level of power and/or a waveform corresponding to a mode of operation associated with the button.

In both example implementations, the electrosurgical energy supplied by the electrosurgical generator 110 can be supplied from (i) the power cord 122, the printed circuit board 132, and/or the switches 138 to (ii) the electrosurgical blade 128 by the helical conductor 134 and the conductive lead(s) 136. As such, as shown in FIG. 1, the printed circuit board 132 can be coupled to the power cord 122, the helical conductor 134 can be coupled to the printed circuit board 132 and the conductive lead(s) 136, and the conductive lead(s) 136 can be coupled to the electrosurgical blade 128. In this arrangement, the helical conductor 134 can conduct the electrosurgical energy (supplied to the helical conductor 134 via the printed circuit board 132) to the conductive lead(s) 136, and the conductive lead(s) 136 can conduct the electrosurgical energy to the electrosurgical blade 128.

As shown in FIG. 1, the printed circuit board 132 and the helical conductor 134 can be located in the housing 124 (e.g., in an internal cavity of the housing 124). The conductive lead(s) 136 can extend along the shaft 126, which can telescopically move relative to the housing 124. The helical conductor 134 is coiled around the shaft 126 in the housing 124. In particular, the shaft 126 can include a proximal portion in the housing 124 and a distal portion that extends outwardly from the housing 124, and the helical conductor 134 can be coiled around the proximal portion of the shaft 126 in the housing 124. As described in further detail below, coiling the helical conductor 134 around the shaft 126 can assist in maintaining electrical communication between upstream electrical components (e.g., the printed circuit board 132, the switches 138, and/or the power cord 122) and downstream electrical components (e.g., the conductive lead(s) 136 and/or the electrosurgical blade 128) as the shaft 126 telescopically moves relative to the housing 124.

In general, the helical conductor 134 can include one or more conductive elements that provide an electrically conductive bus for supplying the electrosurgical energy to the electrosurgical blade 128. In one example, the helical conductor 134 can include a plurality of individual strands of insulated wires coiled into a helical shape. In another example, the helical conductor 134 can include a multiple-wire ribbon cable wound into a helical shape. In yet another example, the helical conductor 134 can include a multiple-conductor flex-circuit cable wound into a helical shape. In each of these examples, the helical conductor 134 can be compressible and expandable such that the helical conductor 134 can accommodate the shaft 126 telescopically moving into and/or out of the housing 124 to retract and/or extend, respectively, the electrosurgical blade 128 relative to the housing 124.

Within examples, the conductive lead(s) 136 can extend from the helical conductor 134 to the electrosurgical blade 128. In one example, the conductive lead(s) 136 can include one or more wires. In another example, the conductive lead(s) 136 can include one or more conductive traces formed by, for instance, screen printing, sputtering, electroplating, and/or laser ablation. The conductive lead(s) 136 can be disposed in an internal conduit of the shaft 126 and an exterior surface of the shaft 126 can be formed of an electrically insulating material. This can help reduce (or prevent) loss of the electrosurgical energy prior to the electrosurgical blade 128.

In some examples, as shown in FIG. 1, the electrosurgical device 112 can additionally include a light source 140 that is configured to emit light. In particular, the light source 140 can be configured to emit light in a distal direction toward a surgical site to illuminate the surgical site while performing electrosurgery using the electrosurgical blade 128. In FIG. 1, the light source 140 is coupled to the shaft 126 (e.g., the light source 140 can be at a distal end of the shaft 126). As such, the light source 140 can also move telescopically with the shaft 126 relative to the housing 124. However, in other examples, the light source 140 can be coupled to the housing 124. As examples, the light source 140 can include one or more light emitting diodes (LEDs), organic light emitting diodes (OLEDs), optical fibers, non-fiber optic waveguides, and/or lenses.

In implementations that include the light source 140, the user input device(s) 130, the printed circuit board 132, the switches 138, the helical conductor 134, and/or the conductive lead(s) 136 can additionally supply an electrical power from a direct current (DC) power source 142 to the light source 140. In one example, the DC power source 142 can include a battery disposed in the housing 124 and/or the plug of the power cord 122. Although the electrosurgical device 112 includes the DC power source 142 in FIG. 1, the DC power source 142 can be separate and distinct from the electrosurgical device 112 in other examples. For instance, in another example, the electrosurgical generator 110 can include the DC power source 142.

Additionally, in implementations that include the light source 140, the user input device(s) 130 can be operable to cause the light source 140 to emit the light. In one example, the user input device(s) 130 can include a button that independently controls the light source 140 separate from the button(s) that control the electrosurgical operational modes of the electrosurgical device 112. In another example, the user input device(s) 130 and the printed circuit board 132 can be configured such that operation of the button(s) that control the electrosurgical operational mode simultaneously control operation of the light source 140 (e.g., the light source 140 can be automatically actuated to emit light when a button is operated to apply the electrosurgical energy at the electrosurgical blade 128).

As shown in FIG. 1, responsive to operation of the user input device(s) 130 to actuate the light source 140, the DC power source 142 can supply the electrical power (e.g., a DC voltage) to the light source 140 via the printed circuit board 132, the helical conductor 134, and/or the conductive lead(s) 136. In this implementation, one or more of the conductive elements of the helical conductor 134 can be configured to supply the electrical power from the DC power source 142 to the light source 140 and/or return the electrical power from the light source 140 to the DC power source 142. Accordingly, the helical conductor 134 can additionally or alternatively assist in providing electrical communication between the DC power source 142 and the light source 140 as the shaft 126 and the light source 140 telescopically move relative to the housing 124.

Figure 2:
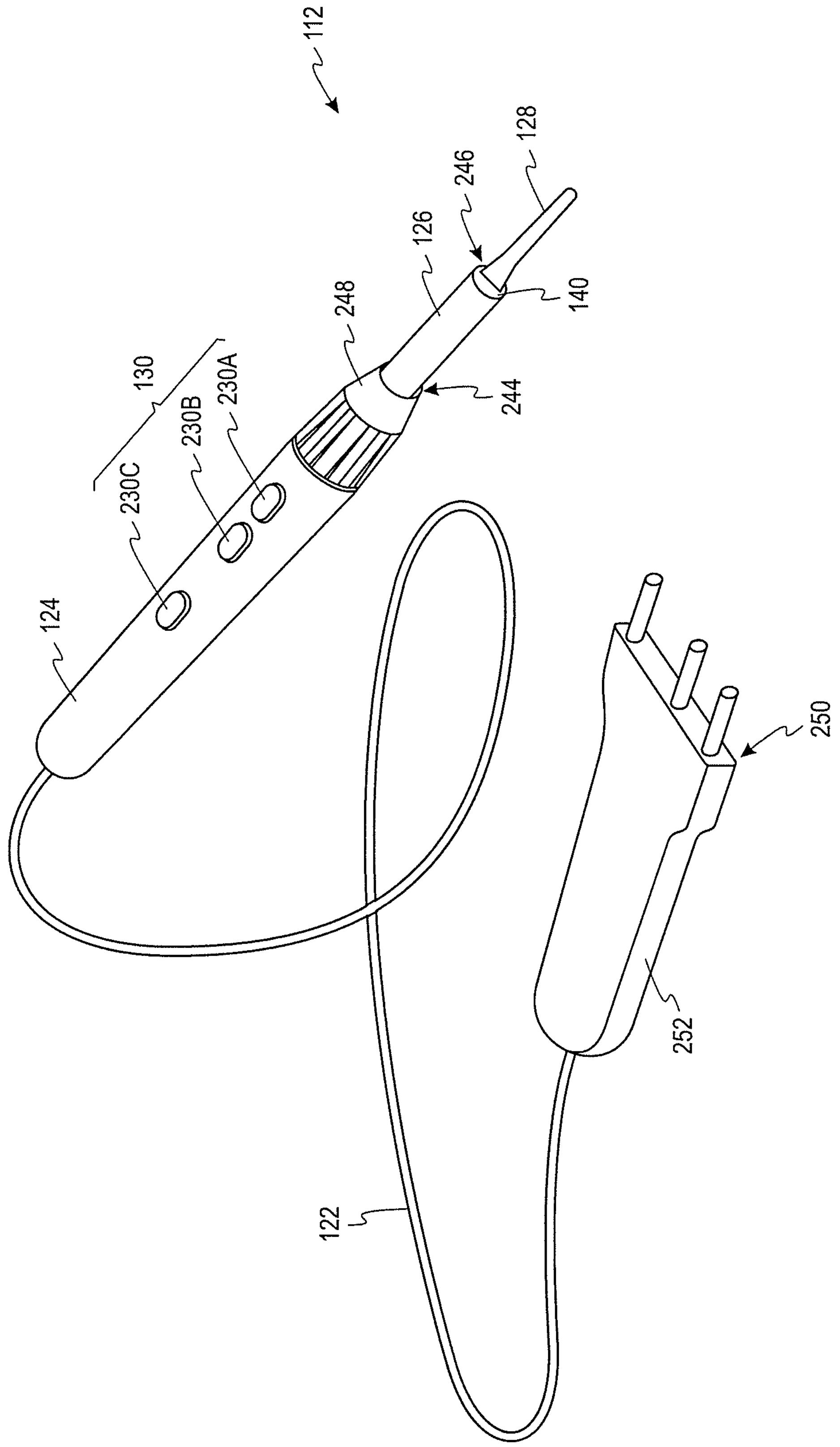
FIG. 2 depicts a perspective view of an electrosurgical device, according to an example.

Referring now to FIG. 2, a perspective view of an implementation of the electrosurgical device 112 is shown according to an example. As shown in FIG. 2, the electrosurgical device 112 includes the housing 124 defining an interior bore 244, the shaft 126 telescopically moveable in the interior bore 244 of the housing 124, and the electrosurgical blade 128 coupled to the shaft 126.

Additionally, in FIG. 2, the light source 140 is at a distal end 246 of the shaft 126. In this arrangement, the light source 140 can telescopically move with the shaft 126 relative to the housing 124. In FIG. 2, the light source 140 surrounds the electrosurgical blade 128. This can help to emit the light in a relatively uniform manner by reducing (or preventing) shadows due to an orientation of the light source 140 and the electrosurgical blade 128 relative to the surgical site. However, in other examples, the light source 140 may not extend entirely around the electrosurgical blade 128 at the distal end 246 of the shaft 126.

In some examples, the electrosurgical device 112 can include a collar 248 at a proximal end of the housing 124. The collar 248 can be rotatable relative to the housing 124 to increase and/or decrease friction between an outer surface of the shaft 126 and an inner surface of the collar 248. In this way, the collar 248 to allow and/or inhibit axial telescopic movement of the shaft 126 relative to the housing 124.

As shown in FIG. 2, the electrosurgical device 112 includes the power cord 122. At a proximal end 250 of the power cord 122, the power cord 122 includes a plug 252 configured to couple to the connector 120 of the electrosurgical generator 110. A distal end of the power cord 122 is coupled to the printed circuit board 132 in an interior cavity of the housing 124. In this arrangement, the power cord 122 extends proximally from the housing 124 to the plug 252.

Additionally, as shown in FIG. 2, the user input device(s) 130 include a first button 230A, a second button 230B, and a third button 230C on an exterior surface of the housing 124. In one implementation, the first button 230A can be actuated to operate the electrosurgical device 112 in a cutting mode of operation, the second button 230B can be actuated to operate the electrosurgical device 112 in a coagulation mode of operation, and the third button 230C can be actuated to operate the light source 140 (i.e., to cause the light source 140 to emit light or cease emitting light). As described above, the user input device(s) 130 can be configured differently in other examples.

Figure 3A:
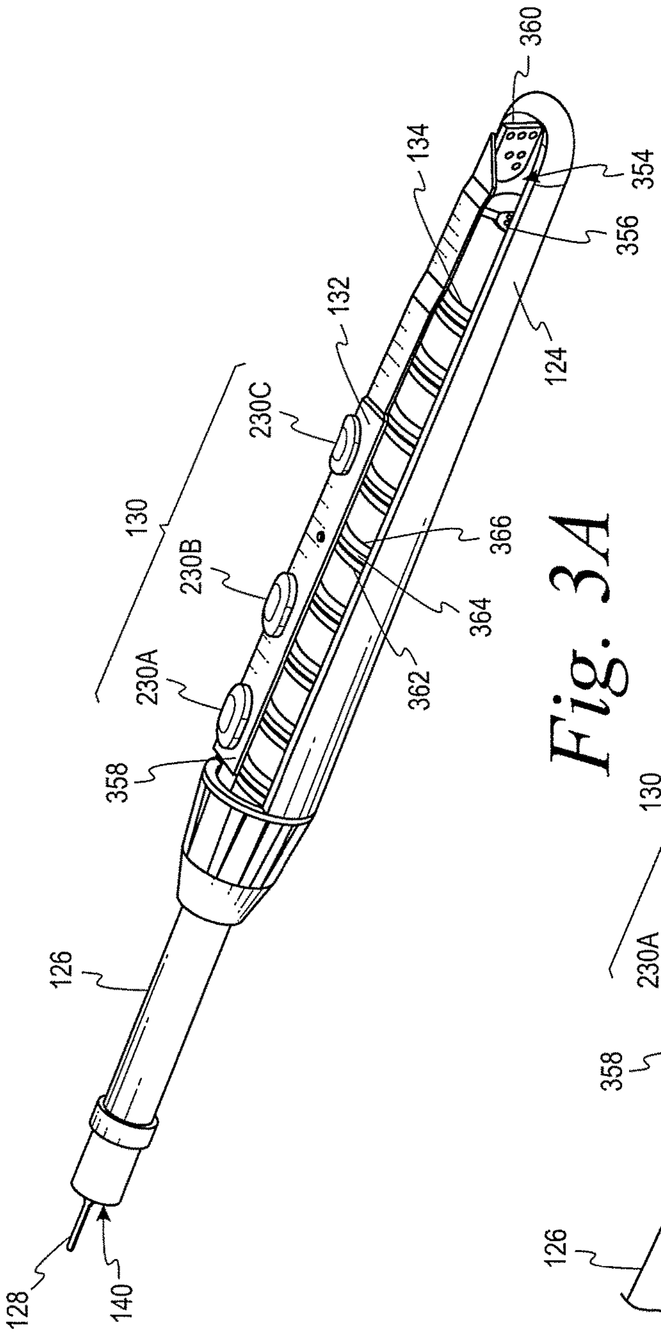
FIG. 3A depicts an electrosurgical device with a shaft in a distal position relative to a housing, according to an example.
Figure 3B:
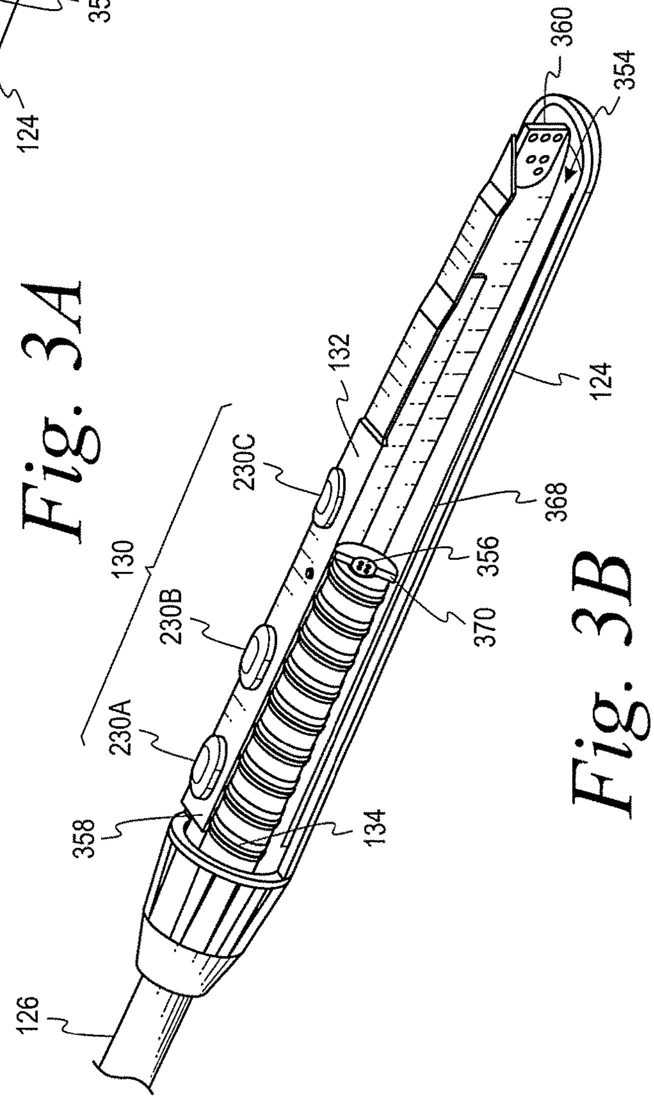
FIG. 3B depicts an electrosurgical device of FIG. 3A with the shaft in a proximal position relative to the housing, according to an example.

FIGS. 3A-3B depict the electrosurgical device 112 with a portion of the housing 124 omitted to facilitate illustration of an interior cavity 354 of the housing 124. In particular, FIG. 3A depicts the electrosurgical device 112 with the shaft 126 in a retracted position relative to the housing 124, and FIG. 3B depicts the electrosurgical device 112 with the shaft 126 in an extended position relative to the housing 124.

As shown in FIGS. 3A-3B, a proximal portion of the shaft 126 is in the interior cavity 354 of the housing 124 and a distal portion of the shaft 126 extends distally from the housing 124. Also, as shown in FIGS. 3A-3B, the helical conductor 134 is coiled around the shaft 126 (e.g., the proximal portion of the shaft 126) and configured to supply electrosurgical energy from an electrosurgical generator 110 to the electrosurgical blade 128.

In FIGS. 3A-3B, a proximal end of the helical conductor 134 is coupled to the proximal portion of the shaft 126 and a distal end of the helical conductor 134 is fixedly coupled to the housing 124 such that when the shaft 126 telescopically moves relative to the housing 124: (i) a position of a distal end of the helical conductor 134 remains fixed relative to the housing 124 and (ii) a position of a proximal end of the helical conductor 134 translates relative to the housing 124. Specifically, in FIGS. 3A-3B, the shaft 126 can include a first terminal 356 at which the proximal end of the helical conductor 134 is electrically coupled to the conductive lead(s) 136. In this way, the proximal end of the helical conductor 134 can be coupled to the conductive lead(s) 136 that extend along the shaft 126 from the proximal portion of the shaft 126 to the electrosurgical blade 128.

Additionally, in FIGS. 3A-3B, the distal end of the helical conductor 134 can be coupled to the printed circuit board 132 at a second terminal 358. The printed circuit board 132 is fixedly coupled to the housing 124. Accordingly, in FIGS. 3A-3B, the distal end of the helical conductor 134 is fixedly coupled to the housing 124 via a printed circuit board 132. The printed circuit board 132 is coupled to the power cord 122 at a third terminal 360.

In this arrangement, the position of a distal end of the helical conductor 134 remains fixed relative to the housing 124 (e.g., at the second terminal 358), whereas the position of a proximal end of the helical conductor 134 (e.g., at the first terminal 356) translates relative to the housing 124 as the shaft 126 telescopically moves relative to the housing 124 between a proximal-most position of the shaft 126 shown in FIG. 3A and a distal-most position of the shaft 126 shown in FIG. 3B. As shown in FIG. 3A, the helical conductor 134 can define a coil having a first diameter when the shaft 126 is in the proximal-most position. As shown in FIG. 3B, the coil can have a second diameter when the shaft 126 is in the distal-most position. In this example, the second diameter is greater than the first diameter. In other words, the diameter of a helical shape defined by the helical conductor 134 can expand and/or retract to accommodate the telescopic movement of the shaft 126 relative to the housing 124 shown in FIGS. 3A-3B.

Additionally, in FIGS. 3A-3B, the helical conductor 134 defines a plurality of turns around the shaft 126, and a spacing between adjacent turns of the plurality of turns is adjusted as the shaft 126 telescopically moves relative to the housing 124 between the positions shown in FIGS. 3A-3B. This can additionally or alternatively help the helical conductor 134 to accommodate the telescopic movement of the shaft 126 relative to the housing 124 shown in FIGS. 3A-3B. In some examples, the helical conductor 134 can include a coating and/or film on an exterior surface that can help to reduce friction between the helical conductor 134 and the shaft 126. For instance, the helical conductor 134 can include a Teflon coating that engages an exterior surface of the shaft 126.

As noted above, the helical conductor 134 can include one or more conducting elements. In FIGS. 3A-3B, the helical conductor 134 includes a plurality of conducting elements. Specifically, in FIGS. 3A-3B, the conducting elements include a first conducting element 362, a second conducting element 364, and a third conducting element 366. The first conducting element 362 is configured to supply the electrosurgical energy to the electrosurgical blade 128. Whereas, the second conducting element 364 and the third conducting element 366 are configured to supply the electrical power to the light source 140.

As noted above, the shaft 126 can be rotatable relative to the housing 124. As shown in FIG. 3B, the electrosurgical device 112 can include a mechanical stop 368 that can limit an extent of rotation of the shaft 126 relative to the housing 124. This can help to mitigate (or prevent) the helical conductor 134 decoupling from the printed circuit board 132 due to the shaft 126 over-rotating relative to the housing 124 and exerting excessive force on the helical conductor 134. In one example, the mechanical stop 368 can limit the extent of rotation of the shaft 126 relative to the housing 124 to approximately 180 degrees of rotation. In implementations in which the electrosurgical blade 128 has a symmetric shape, rotation of the shaft 126 and the electrosurgical blade 128 up to approximately 180 degrees can allow for a the electrosurgical blade 128 to provide a full range of angular orientations of the electrosurgical blade 128 relative to the user input device(s) 130 on the housing 124. However, in other examples, the mechanical stop 368 can limit the extent of rotation of the shaft 126 relative to the housing 124 to approximately 30 degrees of rotation to approximately 360 degrees of rotation.

In FIG. 3B, the mechanical stop 368 includes a first protrusion that extends inwardly from an interior surface of the housing 124 toward the shaft 126. The first protrusion of the mechanical stop 368 can engage with a second protrusion 370 on a proximal end of the shaft 126 when the shaft 126 is in at least one rotational position relative to the housing 124 to prevent further rotation of the shaft 126 relative to the housing 124. The mechanical stop 368 can be configured differently in other examples.

Figure 4A:
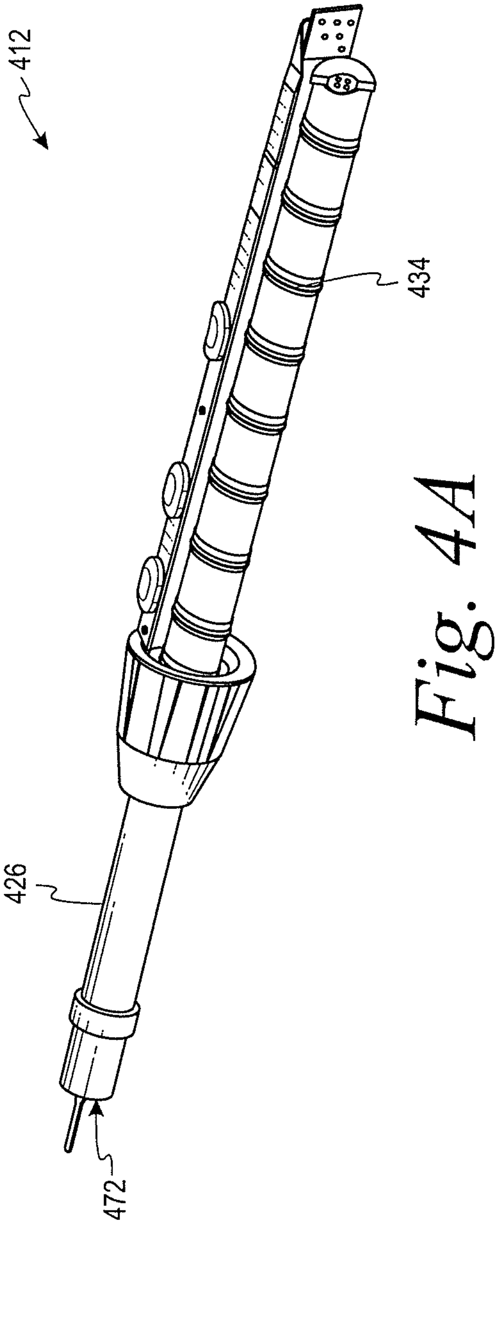
FIG. 4A depicts an electrosurgical device with a shaft in a distal position relative to a housing, according to an example.
Figure 4B:
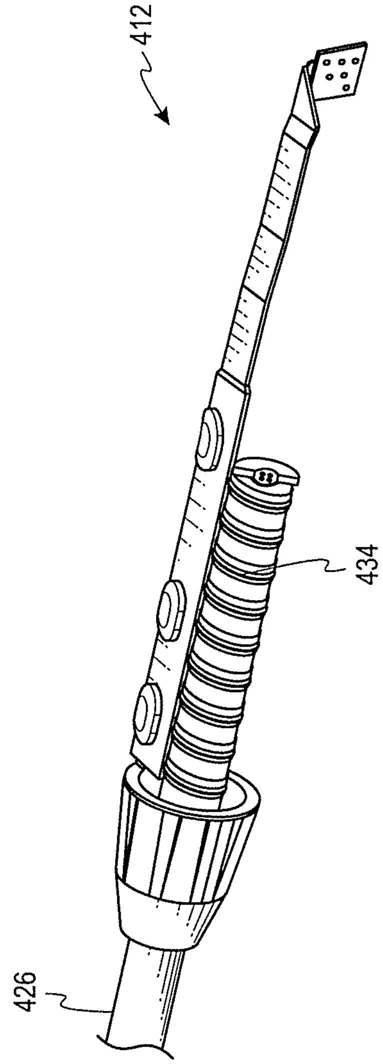
FIG. 4B depicts an electrosurgical device of FIG. 3A with the shaft in a proximal position relative to the housing, according to an example.

Referring now to FIGS. 4A-4B, an electrosurgical device 412 is shown according to another example. The electrosurgical device 412 is substantially similar (or identical) to the electrosurgical device 112 described above, except (i) the electrosurgical device 412 includes a suction port 472 at a distal end of a shaft 426 instead of the light source 140 and (ii) the electrosurgical device 412 includes a helical conductor 434 in the form of a ribbon cable (e.g., a three-wire ribbon cable). In this example, the shaft 426 can include an internal lumen in communication with the suction port 472 and configured to apply a vacuum to the suction port 472 when the internal lumen is coupled to a vacuum source (e.g., via a vacuum tube extending proximally from a housing of the electrosurgical device 412).

In the examples described above, the helical conductor 134, 434 is coiled around the shaft 126, 426 to form a helical shape of the helical conductor 134, 434. As described above, this can allow for the helical conductor 134, 434 to expand and/or retract to accommodate the telescopic movement of the shaft 126, 426 relative to the housing 124. In another example, an electrosurgical device (e.g., the electrosurgical device 112, 412) can include a conductor having a saw-tooth shape coupled to the shaft instead of the helical conductor. The saw-tooth shape of the conductor can facilitate expanding and/or retracting the conductor to accommodate the telescopic movement of the shaft relative to the housing.

Figure 5:
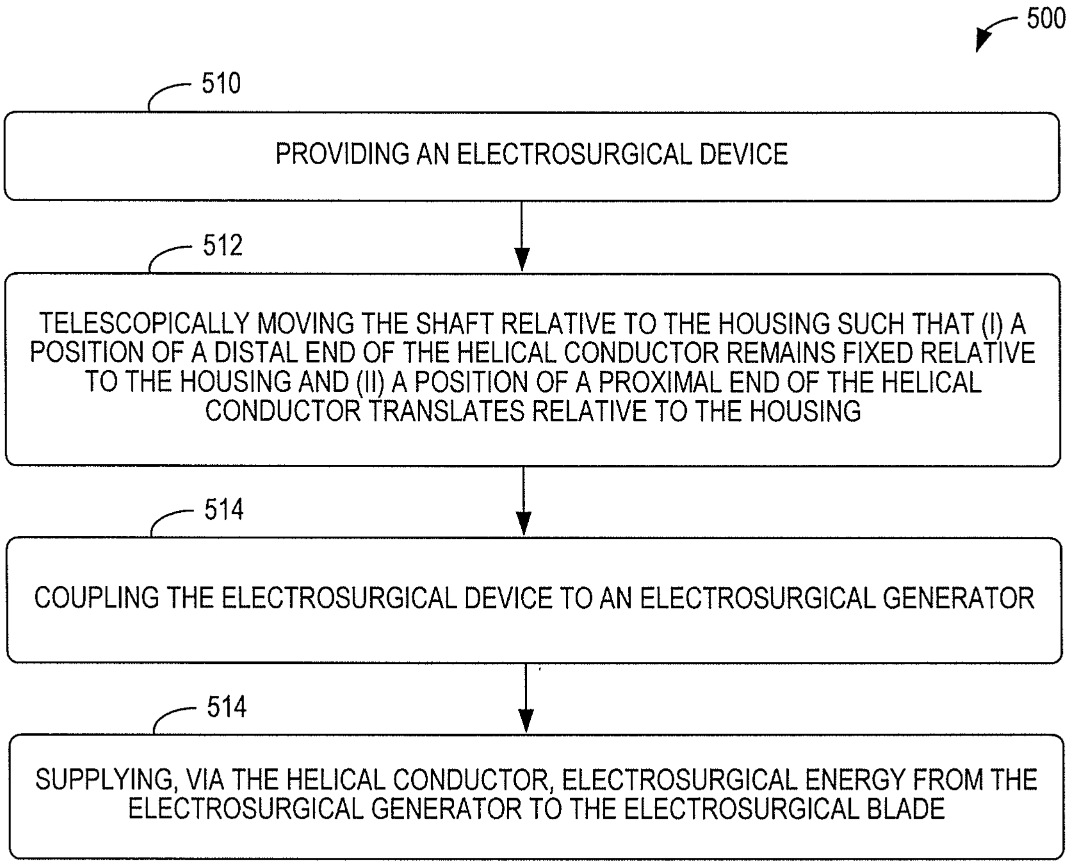
FIG. 5 depicts a flowchart for a method of using an electrosurgical device, according to an example.

Referring now to FIG. 5, a flowchart for a process 500 of using an electrosurgical device is shown according to an example. At block 510, the process 500 can include providing an electrosurgical device. The electrosurgical device can include a housing defining an interior bore, a shaft telescopically moveable in the interior bore of the housing, an electrosurgical blade coupled to the shaft, and a helical conductor coiled around the shaft.

At block 512, the process 500 can include telescopically moving the shaft relative to the housing such that (i) a position of a distal end of the helical conductor remains fixed relative to the housing and (ii) a position of a proximal end of the helical conductor translates relative to the housing. At block 514, the process 500 can include coupling the electrosurgical device to an electrosurgical generator. At block 516, the process 500 can include supplying, via the helical conductor, electrosurgical energy from the electrosurgical generator to the electrosurgical blade.

Figure 6:
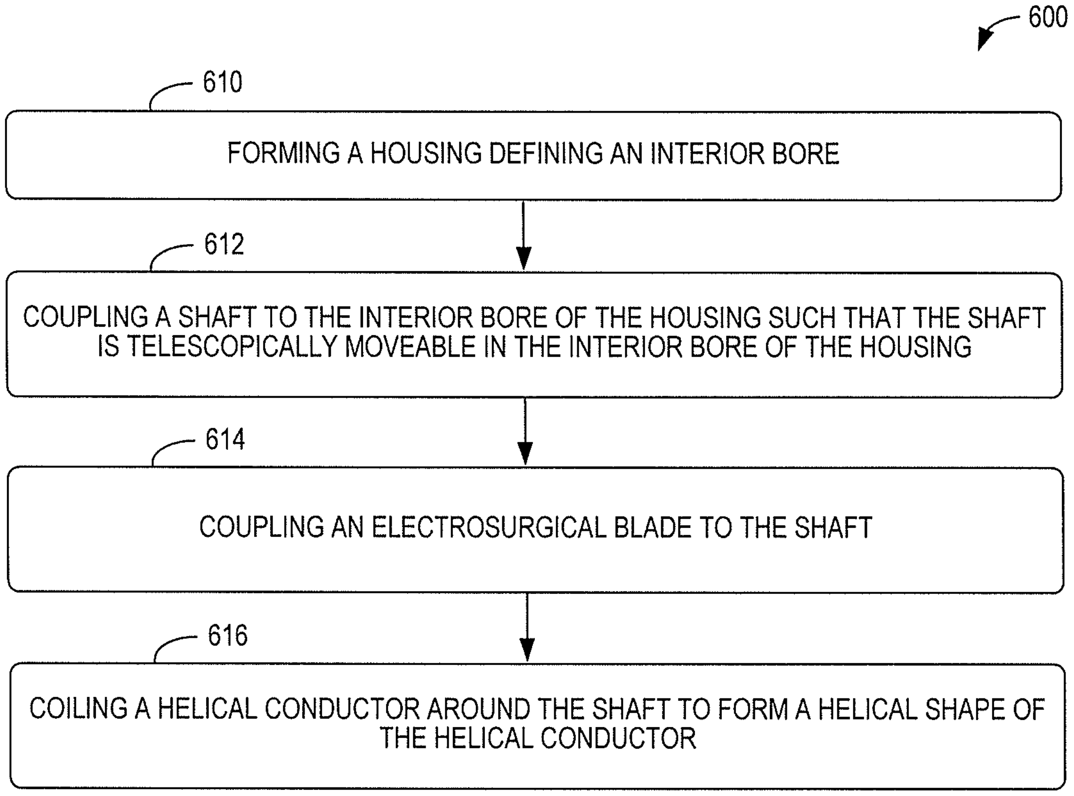
FIG. 6 depicts a flowchart for a method of making an electrosurgical device, according to an example.

Referring now to FIG. 6, a flowchart for a process 600 of making a urine collection device is shown according to an example. As shown in FIG. 6, at block 610, the process 600 includes forming a housing defining an interior bore. At block 612, the process 600 includes coupling a shaft to the interior bore of the housing such that the shaft is telescopically moveable in the interior bore of the housing. At block 614, the process 600 includes coupling an electrosurgical blade to the shaft. At block 616, the process 600 includes coiling a helical conductor around the shaft to form a helical shape of the helical conductor. The helical conductor is configured to supply an electrosurgical energy from an electrosurgical generator to the electrosurgical blade.

Figure 7:
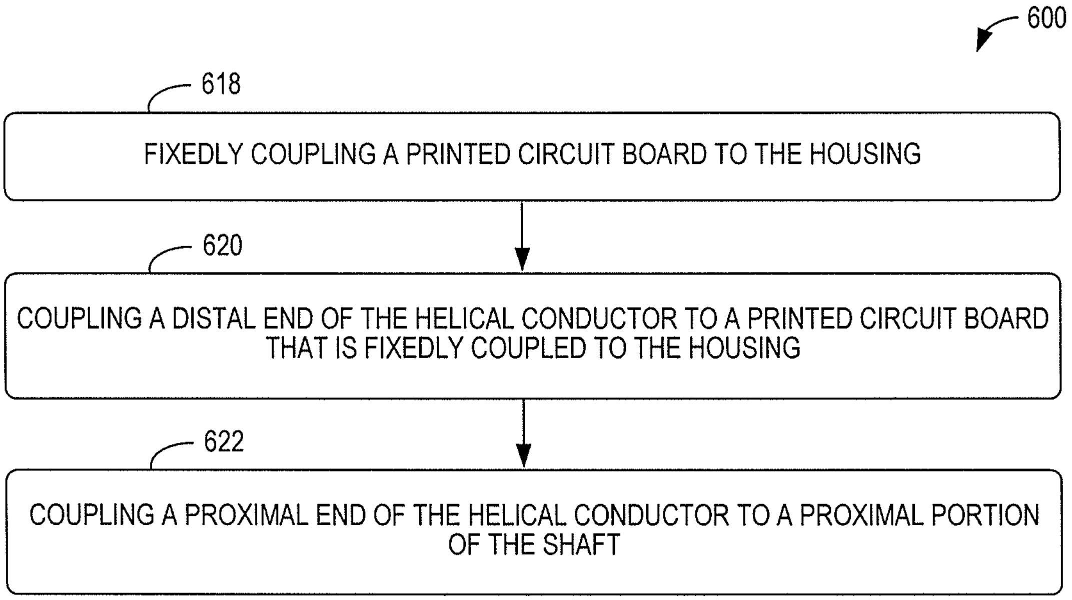
FIG. 7 depicts a flowchart for a method of making an electrosurgical device that can be used with the method of FIG. 6, according to an example.
Figure 8:
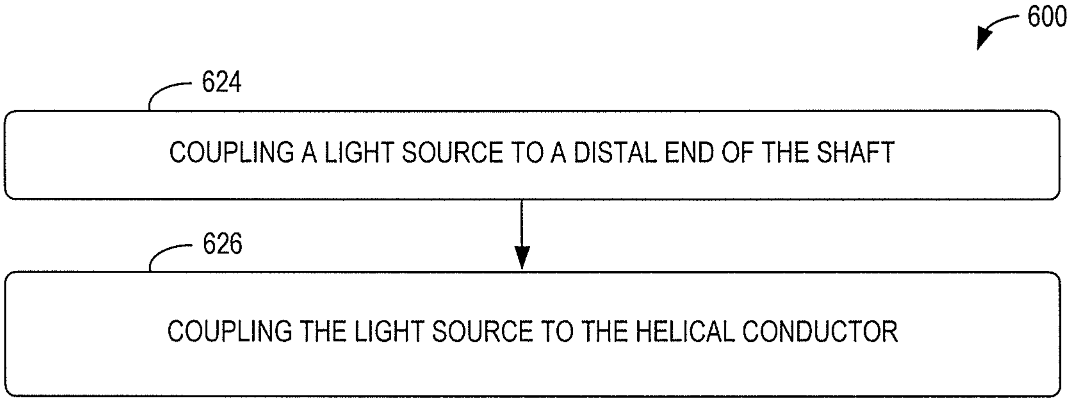
FIG. 8 depicts a flowchart for a method of making an electrosurgical device that can be used with the method of FIG. 6, according to an example.

FIGS. 7-8 depict additional aspects of the process 600 according to further examples. As shown in FIG. 7, the process 600 can also include fixedly coupling a printed circuit board to the housing at block 618, coupling a distal end of the helical conductor to a printed circuit board that is fixedly coupled to the housing at block 620, and coupling a proximal end of the helical conductor to a proximal portion of the shaft at block 622. The printed circuit board can include a plurality of switches that are operable to control a supply of the electrosurgical energy from the electrosurgical generator to the electrosurgical blade.

As shown in FIG. 8, the process 600 can also include coupling a light source to a distal end of the shaft at block 624, and coupling the light source to the helical conductor at block 626.

One or more of the blocks shown in FIGS. 6-8 may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In some instances, components of the devices and/or systems described herein may be configured to perform the functions such that the components are actually configured and structured (with hardware and/or software) to enable such performance. Example configurations then include one or more processors executing instructions to cause the system to perform the functions. Similarly, components of the devices and/or systems may be configured so as to be arranged or adapted to, capable of, or suited for performing the functions, such as when operated in a specific manner.

Further, the disclosure comprises examples according to the following clauses:

Clause 1: An electrosurgical device includes a housing defining an interior bore, a shaft telescopically moveable in the interior bore of the housing, an electrosurgical blade coupled to the shaft, and a helical conductor coiled around the shaft and configured to supply electrosurgical energy from an electrosurgical generator to the electrosurgical blade.

Clause 2: The electrosurgical device of Clause 1, wherein the shaft is rotatable relative to the housing.

Clause 3: The electrosurgical device of Clause 2, further including a mechanical stop configured to limit an extent of rotation of the shaft relative to the housing.

Clause 4: The electrosurgical device of Clause 3, wherein the mechanical stop is configured to limit the extent of rotation of the shaft relative to the housing to approximately 180 degrees of rotation.

Clause 5: The electrosurgical device of Clause 1, wherein a proximal end of the helical conductor is coupled to a proximal portion of the shaft and a distal end of the helical conductor is fixedly coupled to the housing such that when the shaft telescopically moves relative to the housing: (i) a position of a distal end of the helical conductor remains fixed relative to the housing and (ii) a position of a proximal end of the helical conductor translates relative to the housing.

Clause 6: The electrosurgical device of Clause 5, further including a printed circuit board fixedly coupled to the housing. The printed circuit board includes a plurality of switches that are operable to control a supply of the electrosurgical energy from the electrosurgical generator to the electrosurgical blade. The distal end of the helical conductor is coupled to the housing via a printed circuit board.

Clause 7: The electrosurgical device of Clause 6, wherein the printed circuit board is coupled to a power cord, which is configured to be coupled to the electrosurgical generator.

Clause 8: The electrosurgical device of Clause 7, wherein the proximal end of the helical conductor is coupled to a conductive lead that extends along the shaft from the proximal portion of the shaft to the electrosurgical blade.

Clause 9: The electrosurgical device of Clause 1, further including a light source configured to emit light, wherein the helical conductor is configured to supply an electrical power from a direct current (DC) power source to the light source.

Clause 10: The electrosurgical device of Clause 9, wherein the light source is at a distal end of the shaft.

Clause 11: The electrosurgical device of Clause 9, wherein the helical conductor includes a plurality of conducting elements. The plurality of conducting elements include a first conducting element, a second conducting element, and a third conducting element. The first conducting element is configured to supply the electrosurgical energy to the electrosurgical blade. The second conducting element and the third conducting element are configured to supply the electrical power to the light source.

Clause 12: The electrosurgical device of Clause 11, wherein the electrosurgical energy is an alternating current (AC) voltage, and wherein the electrical power is a DC voltage.

Clause 13: The electrosurgical device of Clause 1, wherein the helical conductor includes a ribbon cable.

Clause 14: The electrosurgical device of Clause 1, wherein the shaft is telescopically movable between a proximal-most position relative to the housing and a distal-most position relative to the housing. The helical conductor defines a coil having a first diameter when the shaft is in the proximal-most position. The coil has a second diameter when the shaft is in the distal-most position. The second diameter is greater than the first diameter.

Clause 15: The electrosurgical device of Clause 1, wherein conductor includes a teflon coating that engages an exterior surface of the shaft.

Clause 16: The electrosurgical device of Clause 1, wherein the helical conductor defines a plurality of turns around the shaft. A spacing between adjacent turns of the plurality of turns is adjusted as the shaft telescopically moves relative to the housing.

Clause 17: A method of making an electrosurgical device includes: (i) forming a housing defining an interior bore, (ii) coupling a shaft to the interior bore of the housing such that the shaft is telescopically moveable in the interior bore of the housing, (iii) coupling an electrosurgical blade to the shaft, and (iv) coiling a helical conductor around the shaft to form a helical shape of the helical conductor. The helical conductor is configured to supply an electrosurgical energy from an electrosurgical generator to the electrosurgical blade.

Clause 18: The method of Clause 17, further including fixedly coupling a printed circuit board to the housing. The printed circuit board includes a plurality of switches that are operable to control a supply of the electrosurgical energy from the electrosurgical generator to the electrosurgical blade. The method further includes coupling a distal end of the helical conductor to a printed circuit board that is fixedly coupled to the housing, and coupling a proximal end of the helical conductor to a proximal portion of the shaft.

Clause 19: The method of Clause 17, further including coupling a light source to a distal end of the shaft, and coupling the light source to the helical conductor.

Clause 20: A method of using an electrosurgical device, including providing an electrosurgical device. The electrosurgical device includes a housing defining an interior bore, a shaft telescopically moveable in the interior bore of the housing, an electrosurgical blade coupled to the shaft, and a helical conductor coiled around the shaft. The method also includes telescopically moving the shaft relative to the housing such that (i) a position of a distal end of the helical conductor remains fixed relative to the housing and (ii) a position of a proximal end of the helical conductor translates relative to the housing. The method further includes coupling the electrosurgical device to an electrosurgical generator, and supplying, via the helical conductor, electrosurgical energy from the electrosurgical generator to the electrosurgical blade.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

What is claimed is:

1. An electrosurgical device, comprising:
   a housing defining an interior bore;
   a shaft telescopically moveable in the interior bore of the housing;
   an electrosurgical blade coupled to the shaft;
   a helical conductor coiled around the shaft and configured to supply electrosurgical energy from an electrosurgical generator to the electrosurgical blade,
   wherein a proximal end of the helical conductor is fixedly coupled to a proximal portion of the shaft at a first electrical terminal and a distal end of the helical conductor is fixedly coupled to the housing at a second electrical terminal such that when the shaft telescopically moves relative to the housing: (i) a position of the distal end of the helical conductor remains fixed relative to the housing and (ii) a position of the proximal end of the helical conductor translates relative to the housing,
   wherein the proximal end of the helical conductor is electrically coupled to the first electrical terminal and the distal end of the helical conductor is electrically coupled to the second electrical terminal; and
   a power cord comprising a plug that is configured to couple to the electrosurgical generator,
   wherein the plug is at a proximal end of the power cord and a distal end of the power cord is electrically coupled to a third electrical terminal in the housing such that the power cord is separate and distinct from the helical conductor.

2. The electrosurgical device of claim 1, wherein the shaft is rotatable relative to the housing.

3. The electrosurgical device of claim 2, further comprising a mechanical stop configured to limit an extent of rotation of the shaft relative to the housing.

4. The electrosurgical device of claim 3, wherein the mechanical stop is configured to limit the extent of rotation of the shaft relative to the housing to approximately 180 degrees of rotation.

5. The electrosurgical device of claim 1, wherein the proximal end of the helical conductor is coupled to a proximal end of the shaft.

6. The electrosurgical device of claim 5, further comprising a printed circuit board fixedly coupled to the housing,
   wherein the printed circuit board comprises a plurality of switches that are operable to control a supply of the electrosurgical energy from the electrosurgical generator to the electrosurgical blade, and
   wherein the distal end of the helical conductor is coupled to the housing via the printed circuit board.

7. The electrosurgical device of claim 6, wherein the printed circuit board is coupled to the power cord, which is configured to be coupled to the electrosurgical generator.

8. The electrosurgical device of claim 7, wherein the proximal end of the helical conductor is coupled to a conductive lead that extends along the shaft from the proximal portion of the shaft to the electrosurgical blade.

9. The electrosurgical device of claim 1, further comprising a light source configured to emit light, wherein the helical conductor is configured to supply an electrical power from a direct current (DC) power source to the light source.

10. The electrosurgical device of claim 9, wherein the light source is at a distal end of the shaft.

11. The electrosurgical device of claim 9, wherein the helical conductor comprises a plurality of conducting elements,
   wherein the plurality of conducting elements comprise a first conducting element, a second conducting element, and a third conducting element,
   wherein the first conducting element is configured to supply the electrosurgical energy to the electrosurgical blade, and
   wherein the second conducting element and the third conducting element are configured to supply the electrical power to the light source.

12. The electrosurgical device of claim 11, wherein the electrosurgical energy is an alternating current (AC) voltage, and
   wherein the electrical power is a DC voltage.

13. The electrosurgical device of claim 1, wherein the helical conductor comprises a ribbon cable.

14. The electrosurgical device of claim 1, wherein the shaft is telescopically movable between a proximal-most position relative to the housing and a distal-most position relative to the housing,
   wherein the helical conductor defines a coil having a first diameter when the shaft is in the proximal-most position,
   wherein the coil has a second diameter when the shaft is in the distal-most position, and
   wherein the second diameter is greater than the first diameter.

15. The electrosurgical device of claim 1, wherein the helical conductor defines a plurality of turns around the shaft, and
   wherein a spacing between adjacent turns of the plurality of turns is adjusted as the shaft telescopically moves relative to the housing.

16. A method of making an electrosurgical device, comprising:
   forming a housing defining an interior bore;
   coupling a shaft to the interior bore of the housing such that the shaft is telescopically moveable in the interior bore of the housing;
   coupling an electrosurgical blade to the shaft;
   coiling a helical conductor around the shaft to form a helical shape of the helical conductor; and
   fixedly coupling a proximal end of the helical conductor to a proximal portion of the shaft at a first electrical terminal and fixedly coupling a distal end of the helical conductor to the housing at a second electrical terminal such that when the shaft telescopically moves relative to the housing:
(i) a position of the distal end of the helical conductor remains fixed relative to the housing and
(ii) a position of the proximal end of the helical conductor translates relative to the housing,
   wherein the helical conductor is configured to supply an electrosurgical energy from an electrosurgical generator to the electrosurgical blade,
   wherein the proximal end of the helical conductor is electrically coupled to the first electrical terminal and the distal end of the helical conductor is electrically coupled to the second electrical terminal, wherein the electrosurgical device comprises a power cord including a plug that is configured to couple to the electrosurgical generator, and wherein the plug is at a proximal end of the power cord and a distal end of the power cord is electrically coupled to a third electrical terminal in the housing such that the power cord is separate and distinct from the helical conductor.

17. The method of claim 16, further comprising:

fixedly coupling a printed circuit board to the housing, wherein the printed circuit board comprises a plurality of switches that are operable to control a supply of the electrosurgical energy from the electrosurgical generator to the electrosurgical blade;

coupling the distal end of the helical conductor to the printed circuit board.

18. The method of claim 16, further comprising:

coupling a light source to a distal end of the shaft; and coupling the light source to the helical conductor.

19. A method of using an electrosurgical device, comprising:

providing an electrosurgical device comprising:

a housing defining an interior bore, a shaft telescopically moveable in the interior bore of the housing, an electrosurgical blade coupled to the shaft, a helical conductor coiled around the shaft, and a power cord comprising a plug that is configured to couple to an electrosurgical generator;

telescopically moving the shaft relative to the housing such that (i) a position of a distal end of the helical conductor remains fixed relative to the housing and (ii) a position of a proximal end of the helical conductor translates relative to the housing, wherein the proximal end of the helical conductor is fixedly coupled to a proximal portion of the shaft at a first electrical terminal and the distal end of the helical conductor is fixedly coupled to the housing at a second electrical terminal, wherein the proximal end of the helical conductor is electrically coupled to the first electrical terminal and the distal end of the helical conductor is electrically coupled to the second electrical terminal, and wherein the plug is at a proximal end of the power cord and a distal end of the power cord is electrically coupled to a third electrical terminal in the housing such that the power cord is separate and distinct from the helical conductor;

coupling the plug of the electrosurgical device to the electrosurgical generator; and supplying, via the helical conductor, electrosurgical energy from the electrosurgical generator to the electrosurgical blade.

20. The electrosurgical device of claim 1, wherein the shaft comprises a distal portion that extends outwardly from the housing, wherein the helical conductor is coiled around the proximal portion of the shaft, wherein the shaft is telescopically movable between a proximal-most position relative to the housing and a distal-most position relative to the housing, wherein a helical shape of the helical conductor is configured to define a coil having (i) a first diameter when the shaft is in the proximal-most position and (ii) a second diameter when the shaft is in the distal-most position, wherein the second diameter is greater than the first diameter.

* * * * *